(12) United States Patent
Forrest

(10) Patent No.: US 7,322,961 B2
(45) Date of Patent: Jan. 29, 2008

(54) SEAL ASSEMBLY FOR ELASTOMERIC INFUSION PUMP

(75) Inventor: Kevin M. Forrest, Rancho Santa Margarita, CA (US)

(73) Assignee: I-Flow Corporation, Lake Forest, CA (US)

( * ) Notice: Subject to any disclaimer, the term of this patent is extended or adjusted under 35 U.S.C. 154(b) by 844 days.

(21) Appl. No.: 10/345,343

(22) Filed: Jan. 15, 2003

(65) Prior Publication Data

US 2004/0138627 A1  Jul. 15, 2004

(51) Int. Cl.
A61M 37/00 (2006.01)

(52) U.S. Cl. .................... 604/132; 604/93.01

(58) Field of Classification Search ........... 604/406, 604/404, 403, 408, 410, 327, 317, 132, 131, 604/93.01, 48, 19, 250; 277/904
See application file for complete search history.

(56) References Cited

U.S. PATENT DOCUMENTS

| 1,823,061 | A |   | 9/1931  | Pearson |
|-----------|---|---|---------|---------|
| 3,083,041 | A | * | 3/1963  | Owenmark ............... 285/7 |
| 4,382,579 | A | * | 5/1983  | Morris .................. 251/214 |
| 4,961,743 | A | * | 10/1990 | Kees et al. ............... 606/158 |
| 5,080,652 | A |   | 1/1992  | Sancoff et al. |
| 5,263,940 | A |   | 11/1993 | Kriesel |
| 5,284,481 | A | * | 2/1994  | Soika et al. ............. 604/132 |
| 5,480,394 | A | * | 1/1996  | Ishikawa ................. 604/327 |
| 5,529,214 | A |   | 6/1996  | Lasonde et al. |
| 5,599,328 | A |   | 2/1997  | Stevens |
| 5,611,576 | A |   | 3/1997  | Guala |
| 5,713,860 | A | * | 2/1998  | Kaplan et al. ......... 604/103.01 |
| 5,730,153 | A | * | 3/1998  | Chang et al. ............ 128/846 |
| 5,836,933 | A | * | 11/1998 | Buttitta et al. ........... 604/403 |
| 5,879,143 | A | * | 3/1999  | Cote et al. ............... 417/474 |
| 6,179,558 | B1 | * | 1/2001 | Eastman et al. .......... 415/121.2 |
| 6,773,427 | B2 | * | 8/2004 | Takagi .................... 604/415 |
| 6,854,888 | B1 | * | 2/2005 | Brown et al. ............ 383/80 |
| 2002/0107500 | A1 | * | 8/2002 | Takagi ................ 604/406 |

FOREIGN PATENT DOCUMENTS

WO    WO 02/22189 A1    3/2002

* cited by examiner

Primary Examiner—Nicholas D. Lucchesi
Assistant Examiner—Laura Bouchelle
(74) Attorney, Agent, or Firm—Knobbe, Martens, Olson & Bear LLP

(57) ABSTRACT

An infusion apparatus including a support member and an elastic sleeve surrounding the support member to define a fluid reservoir therebetween. The sleeve is expandable in a radial direction when the infusion apparatus is loaded with a fluid, such as a pain medication, and exerts a pressure on the fluid so that it may be delivered to a desired site, such as a surgical region of a patient. The elastic sleeve is sealed to the support member at spaced-apart locations by first and second sealing arrangements. Each sealing arrangement preferably includes a sealing member having a first end, a second end, and a body portion extending between the first and second ends. Desirably, the body portion is substantially annular in shape and is deflectable between a first inner diameter and a second inner diameter. The first inner diameter permits the sealing member to be passed over an end of the support and elastic sleeve, while the second inner diameter is configured to produce a force tending to create a fluid tight seal between the elastic sleeve and the support.

5 Claims, 2 Drawing Sheets

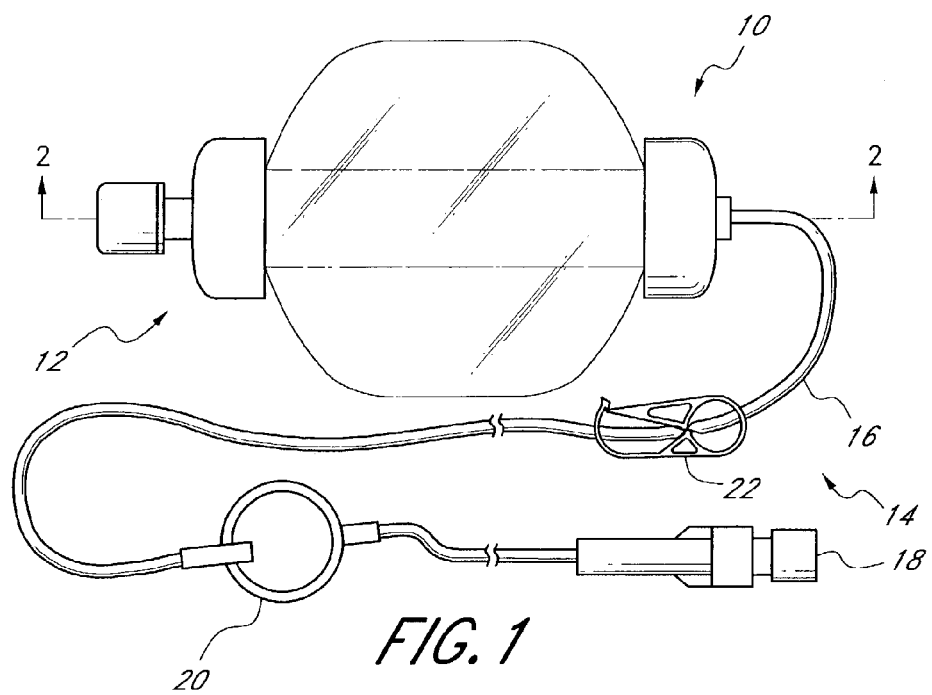
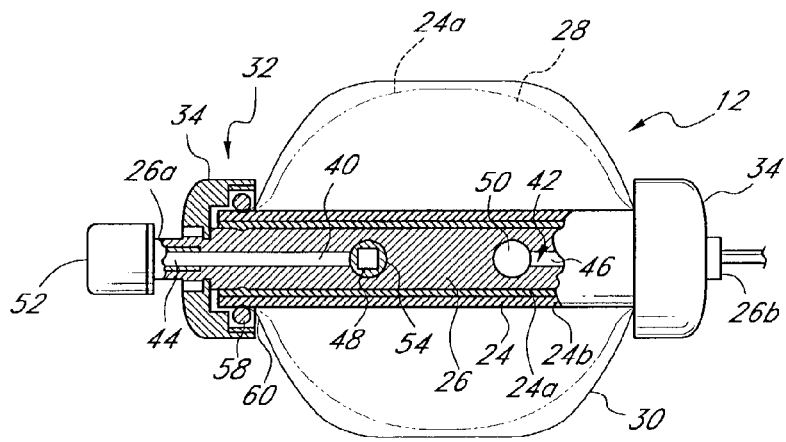
FIG. 2
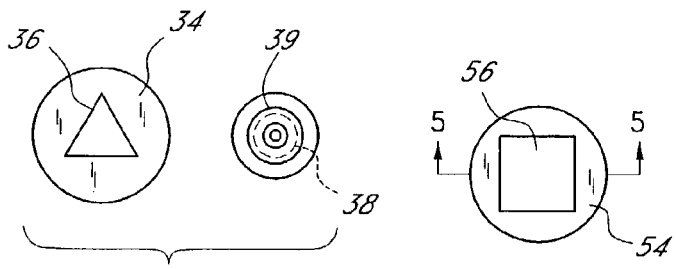
FIG. 3   FIG. 4
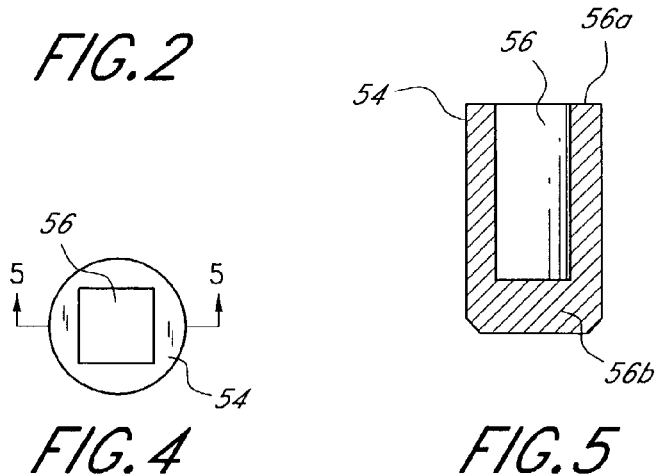
FIG. 5

SEAL ASSEMBLY FOR ELASTOMERIC INFUSION PUMP

BACKGROUND OF THE INVENTION

1. Field of the Invention

The present invention generally relates to liquid infusion systems. More particularly, the present invention relates to a sealing arrangement for a fluid reservoir of an infusion pump. The sealing arrangement provides increased reliability in the seal between the components of the infusion pump creating the fluid reservoir.

2. Description of the Related Art

Frequently in the healthcare field, it is desirable to provide a patient with a solution, medicine, drug, or other substance, on a continuous basis for a period of time. For example, after a surgical procedure, it may be desirable to administer a liquid pain medication to the patient at a controlled rate, over a significant amount of time. In such situations, it may be desirable that this be accomplished while the patient is in an ambulatory state. A variety of portable infusion devices have been developed to accomplish this purpose.

One common portable infusion device is referred to as an elastomeric infusion pump. An elastomeric infusion pump typically utilizes one or more elastic sleeves mounted over a cylindrical support member. The elastic sleeve is sealed to the support member at both ends and a drug, or other substance to be infused, is introduced into a space, or reservoir, between the sleeve and the support member. As the infusion pump is being loaded with the drug, the elastic sleeve expands in a generally radial direction about the support member. While in an expanded condition, the elastic sleeve exerts a pressure on the drug, which forces the drug through an outlet of the elastomeric pump. A delivery device, such as a catheter, is in fluid communication with the elastomeric pump to deliver the pressurized drug to the patient.

Importantly, a secure seal must be created and maintained between the elastic sleeve and the support member to ensure proper and reliable operation of the elastomeric pump. An annular member, or O-ring, made from an elastic material, is often used to create a seal between the elastic sleeve and the support member. Under ideal conditions, a properly sized and installed O-ring may exert a sufficient force on the elastic sleeve to create and maintain a seal between the sleeve and the support member. However, elastic, O-ring type sealing members possess certain disadvantages, making them less than ideal under actual use conditions.

For example, an O-ring sealing member relies on inherent elasticity to be capable of increasing from its nominal diameter, in order to be assembled onto the combination of the support member and sleeve. Further, the O-ring relies on inherent elasticity to return toward its nominal diameter and, thus, apply a sealing force to the elastic sleeve. Accordingly, physical properties and dimensions of the O-ring sealing member influence the predictability and reliability of the seal.

However, due to normal manufacturing variations, certain physical dimensions of an O-ring sealing member, such as the inner diameter, may vary significantly from a desired, nominal value. Such variations may result in the O-ring, if the inner diameter is significantly smaller than the nominal value, being difficult to assemble over the elastic sleeve and support member. Conversely, if the inner diameter is too large, the O-ring may not exert a sufficient force on the elastic sleeve to create a secure seal between the sleeve and the support member.

Furthermore, common materials used to produce O-rings having a desirable amount of elasticity tend to have a relatively soft outer surface and may be easily damaged during handling, assembly and normal usage. Surface damage to an O-ring type sealing member, such as small cuts or tears, may result in failure of the O-ring and resulting failure of the elastomeric pump. In addition, imperfections in the raw material or the manufacturing process may result in premature failure of the O-ring.

SUMMARY OF THE INVENTION

Accordingly, preferred embodiments of the present seal assembly desirably provide a secure, reliable seal between the elastic sleeve and the support member of an elastomeric infusion pump. Preferably, the seal assembly is resistant to damage during manufacture, handling and use.

An aspect of the present invention involves an infusion apparatus including a cylindrical support member having an outer surface. A first annular groove and a second annular groove are defined by the outer surface and spaced from one another. A reservoir wall of the support member is defined between the annular grooves. The apparatus also includes an elastic sleeve surrounding the reservoir wall of the support member and covering the first and second annular grooves. The sleeve is expandable such that the sleeve and the reservoir wall of the support member cooperate to define a variable volume fluid reservoir. The infusion apparatus includes an inlet and an outlet in fluid communication with the fluid reservoir. A sealing arrangement includes a first sealing member for sealing a first end of the fluid reservoir and a second sealing member for sealing a second end of the fluid reservoir. Each sealing member is of a non-continuous, generally annular shape and includes a first end, a second end, and a body portion extending between the first and second ends. The sealing member is substantially inelastic along the length of the body portion and defines an annular, protruding inner surface complementary to the respective first or second groove. The sealing member is capable of deflecting between a first inner diameter and a second inner diameter, wherein the first inner diameter is sized to permit the sealing member to pass over the sleeve and support, and the second inner diameter is sized to produce a force tending to create a fluid-tight seal between the support and the sleeve.

Another aspect of the present invention involves an infusion apparatus including an infusion pump. The infusion pump includes an elastic sleeve surrounding a cylindrical support member. The sleeve and the support member cooperate to define a variable volume fluid reservoir therebetween. Each end portion of an outer surface of the support member defines an annular groove. Each end of the elastic sleeve extends over the respective groove. The infusion pump includes an inlet and an outlet in fluid communication with the fluid reservoir. The infusion apparatus also includes a pair of spring clips, each clip being associated with one of the annular grooves to create a seal between the elastic sleeve and the support member to define first and second ends, respectively, of the fluid reservoir. Each of the spring clips includes a first end, a second end, and a generally annular body portion extending between the first and second ends. Each of the spring clips is deflectable to a deflected position. The spring clip defines a first inner diameter in a deflected position sized to permit the clip to pass over an end of the infusion pump. Further, the spring clip defines a second inner diameter, smaller than the first diameter, sized to create a fluid-tight seal between the support member and the sleeve.

A further aspect of the present invention involves a method of assembling an infusion apparatus including providing a cylindrical support member at least partially defining an inlet and an outlet. Positioning an elastic sleeve over the support member, thereby defining a variable volume fluid reservoir between the support member and the sleeve. The inlet and the outlet communicate with the fluid reservoir. The method further includes providing a pair of spring clips, each clip having a first end, a second end and a generally annular body portion extending between the first and second ends. The method includes applying an opposing force to each of the first and second ends of one of the spring clips to deflect the spring clip into a deflected position and passing the spring clip over a first end of the support member and sleeve. Releasing the first and second ends to permit the body portion to contact the sleeve and create a seal between the sleeve and the support member and thereby define a first end of the fluid reservoir. The method further includes applying an opposing force to each of the first and second ends of the other of the spring clips to deflect the spring clip into a deflected position and passing the spring clip over a second end of the support member and the sleeve. Releasing the first and second ends to permit the body portion to contact the sleeve and create a seal between the sleeve and the support member and thereby define a second end of the fluid reservoir. Preferably, the method also includes trimming the first and second ends to a length shorter than their initial length after the respective spring clip is positioned on to the support member and sleeve.

Still another aspect of the present invention involves an infusion apparatus including an infusion pump having an elastic sleeve surrounding a cylindrical support member. The sleeve and the support member cooperate to define a variable volume fluid reservoir therebetween. The infusion pump includes an inlet and an outlet in fluid communication with the fluid reservoir. The apparatus also includes a pair of sealing assemblies, each assembly creating a seal between the elastic sleeve and the support member to define first and second ends, respectively, of the fluid reservoir. Each of the assemblies comprises a split ring and a cap. The split ring has a first end, a second end, and a generally annular body portion extending between the first and second ends. The split ring is deflectable to an inner diameter sufficient to permit the split ring to pass over an end of the infusion pump. The cap is configured to apply a compressive force to the split ring, thereby deflecting the split ring to an inner diameter sufficient to create a seal between the elastic sleeve and the support member and define an end of the fluid reservoir.

BRIEF DESCRIPTION OF THE DRAWINGS

These and other features, aspects and advantages of the present invention will now be described in relation to drawings of preferred embodiments, which are intended to illustrate and not to limit the present invention. The drawings comprise eight figures.

FIG. 1 is a top plan view of a preferred infusion apparatus.

FIG. 2 is a partial cross-sectional view of the infusion apparatus of FIG. 1 taken along line 2-2 in FIG. 1.

FIG. 3 is an enlarged view of the end cap and coupling portion of the cylindrical support of the infusion apparatus of FIG. 1.

FIG. 4 is an enlarged plan view of a check valve assembly of the infusion apparatus of FIG. 1.

FIG. 5 is a cross-sectional view of the one way valve assembly of FIG. 4 taken along line 5-5 of FIG. 4.

DETAILED DESCRIPTION OF THE PREFERRED EMBODIMENTS

Figure 6:
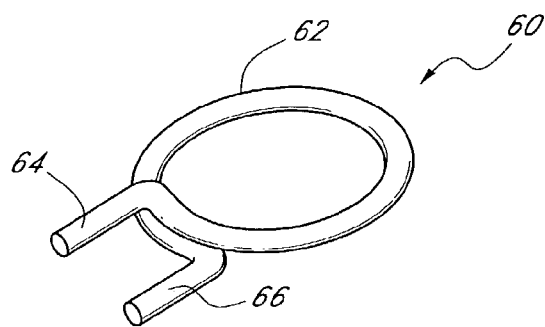
FIG. 6 is a perspective view of the spring clip of FIG. 2 shown separate from the infusion apparatus.

FIGS. 1 and 2 illustrate a preferred embodiment of an infusion apparatus, generally referred to by the reference numeral 10. As described above, the infusion apparatus 10 is operable to deliver a pressurized liquid, such as a pain medication, to a suitable delivery system, such as a catheter (not shown). Preferably, the infusion apparatus 10 is relatively inexpensive, portable and provides reliable operation throughout its useful life. The infusion apparatus 10 may be reusable or may be disposable after a single use.

The infusion apparatus 10 desirably includes an infusion pump 12, which is configured to hold a pressurized supply of a fluid, such as a liquid drug. Preferably, a supply arrangement 14, comprised in substantial part by a length of medical tubing 16, is in fluid communication with the infusion pump 12 at a first end. The supply arrangement 14 supplies the pressurized fluid to the catheter or other delivery device, through an appropriate connection device 18 at a second end. The medical tubing 16 may be formed of any of a variety of materials suitable for use in medical applications. Preferably, such materials are polymeric and substantially chemically inert. Similarly, the connector 18 may be any suitable device to permit relatively quick and secure connection between a pair of medical devices, such as a luer lock, for example. Other types of suitable connectors may also be used.

Desirably, the supply arrangement 14 includes a filter 20 in serial connection with the medical tubing 16. The filter 20 desirably is configured to remove impurities, including air bubbles, from the fluid delivered from the infusion pump 12. The filter 20 may be any suitable medical filter, as is well known in the art.

Preferably, the supply arrangement 14 also includes a clamp 22, which is desirably positioned upstream of the filter 20. The clamp 22, in a closed position, is configured to apply a squeezing pressure to the medical tube 16 to close the lumen therein and occlude fluid flow beyond the clamp 22. Any suitable type of medical clamp may be used.

With reference to FIG. 2, the infusion pump 12 is generally comprised of an elastic sleeve 24 surrounding a support member 26. Preferably, the support member 26 is generally cylindrical in shape, however, other suitable shapes of support members may also be used. The elastic sleeve 24 is expandable in a radial direction about the cylindrical support member 26 to an expanded condition 24a. In the expanded condition 24a, the elastic sleeve 24 and the support member 26 cooperate to define a variable volume fluid reservoir 28 therebetween.

Preferably, the infusion pump 12 is configured such that the reservoir 28 may be filled (also referred to as "loading" the pump 12), from an inlet end 26a of the support member 26. As is described in greater detail below, preferably the pump 12 may be manually loaded with a loading device, such as a syringe. Once the reservoir 28 has been filled with fluid, the elastic nature of the sleeve 24 exerts a pressure on the fluid within the reservoir 28, permitting the fluid to be delivered to a desired site through the supply arrangement 14 and delivery device (not shown).

The sleeve 24 may be comprised of a single layer. However, preferably the sleeve 24 includes multiple layers, or sleeve members, in order to achieve desired overall properties of the sleeve 24. For example, an inner sleeve 24a may comprise a chemically inert material to avoid interaction with the drug within the infusion pump 12 while an outer sleeve 24b may comprise a material having desirable elastic properties. The combination of the sleeves 24a, 24b desirably provide satisfactory elastic properties and desirable chemical properties to consistently and safely deliver the pressurized fluid, such as a pain medication. In one arrangement, the inner sleeve 24a may comprise a semi-elastic thermal plastic material such as KRATON, which has FDA approval for use in medical applications. The outer sleeve 24b may comprise a natural latex rubber material, which provides desirable elastic characteristics. However, other suitable materials may also be used, as may be determined by one of skill in the art.

If desired, the infusion pump 12 may also include a protective, collapsible housing, or pouch 30 surrounding the elastic sleeve 24. Desirably, the pouch 30 is relatively inelastic to limit expansion of the sleeve 24. In addition, the pouch 30 desirably is made from a tougher material than that of the sleeve 24 in order to protect the sleeve from punctures, or other damage. In one preferred arrangement, the pouch 30 is comprised of a pair of flat, sheet-like portions bonded to one another around their peripheral edges. Preferably, the portions of the pouch 30 comprise a PVC material, which are bonded to one another by Radio Frequency (RF) welding. Such a construction provides a suitable, economical means to protect the elastic sleeve 24 from damage. Other suitable materials and construction techniques may also be employed.

Desirably, the elastic sleeve 24 is sealed to the cylindrical support member 26 at spaced apart locations near each end 26a, 26b of the cylindrical support 26 by a pair of seal assemblies 32 (only one shown). Thus, the reservoir 28 of the infusion pump 12 is defined between the pair of seal assemblies 32. If a housing, or pouch 30 is provided, end portions thereof may also be held in place by the seal arrangement 32. These and other details of the sealing arrangements 32 are described in greater detail below.

Desirably, a cap 34 is attached to each end of the infusion pump 12. Preferably, each cap 34 includes a side wall portion which at least partially covers the sealing arrangement 32. Such an arrangement serves to inhibit damage to the sealing arrangement 32 during normal use of the infusion apparatus 10 and provides an aesthetically pleasing outward appearance.

With additional reference to FIG. 3, desirably, the cap 34 is removably connectable to the support member 26. In a preferred embodiment, the cap 34 is coupled to the support member 26 by a snap fit arrangement wherein the cap 34 includes a triangular-shaped cutout 36. The cutout 36 is sized such that a portion of each side of the triangular-shaped cutout 36 may be received within an annular recess 38 defined by the cylindrical support member 26. Desirably, the cap 34 is constructed from a material having sufficient flexibility such that the side portions of the cutout 36 may deflect to pass over the end portion 39 of the support member 26, which has a larger diameter and is positioned outwardly, along the support member 26, from the recess 38. Any of a variety of common thermoplastic materials may be suitable for use in construction of the end cap 34. Although such an arrangement is preferred, other suitable end cap constructions may also be used, such as a threaded end cap arrangement, for example.

The infusion pump 12 also includes an inlet 40 and an outlet 42 in fluid communication with the reservoir 28. In the illustrated embodiment, the inlet and outlet 40, 42 are at least partially defined by the support member 26. Desirably, each of the inlet and outlet 40, 42 include a longitudinally extending channel 44, 46, respectively, which open to opposing end surfaces of the support member 26. In addition, each of the inlet and outlet 40, 42 include a radially extending channel 48, 50, respectively, which communicate with the longitudinal channels 44, 46 and open from a portion of the side wall of the cylindrical member 26 located within the fluid reservoir 28, or the reservoir wall.

The inlet-defining end 26a of the support member 26 desirably is configured to receive a reservoir loading device, such as a syringe, which may be interconnected to the support member 26 by a threaded connection, such as a luer lock connection, for example. In operation, the loading device introduces fluid into the fluid reservoir 28, against the biasing force of the sleeve 24. Desirably, once the infusion pump 12 has been loaded with fluid, the inlet end of the support member 26 is closed by a cap 52. The elasticity of the sleeve 24, once expanded 24a, pressurizes the fluid within the reservoir 28.

Preferably, the inlet 40 includes a one-way valve to inhibit fluid within the reservoir 28 from escaping through the inlet 40. In the illustrated embodiment, the valve includes a valve member 54 positioned within the radially extending channel 48. The valve member 54 is desirably cylindrical in shape and includes a recess 56 extending, from an end surface 56a, along a longitudinal axis of the valve member 54. Preferably, the recess 56 is generally square in cross-section and extends substantially the entire length of the valve member 54, thereby defining a closed end 56b of the member 54 having a thickness approximately equal to a thickness of the outer wall portion of the member 54.

When installed in the radially extending channel 48, a portion of the wall of the valve member 54 facing the longitudinal channel 44 collapses in response to fluid being loaded in the infusion pump 12 through the inlet 40. However, once the fluid pressure within the inlet 40 is lower than the pressure within the reservoir 28 (i.e., filling of the reservoir 28 has ceased), fluid within the recess 56 urges the valve member 54 back into its original, cylindrical orientation to inhibit fluid from entering the longitudinal channel 44 and, thus, exiting the reservoir 28 through the inlet 40. Although such a valve arrangement is preferred for its simplicity and reliable operation, other suitable one-way valves may also be used.

Desirably, the longitudinal channel 46 of the outlet 42 extends through an outlet end 26b of the support member 26 and communicates with the medical tubing 16 of the supply arrangement 14. Desirably, the outlet 42 permits relatively unobstructed fluid flow. That is, a one-way valve mechanism is not necessary or desirable in connection with the outlet 42. Accordingly, with such an arrangement, fluid flow from the reservoir 28 through the outlet 42 is selectively permitted by the clamp 22 of the supply arrangement 14.

In addition, preferably the pump 12 includes a flow restrictor (not shown) downstream from the fluid reservoir 28. Desirably, the flow restrictor is configured to restrict the flow rate of fluid exiting the fluid reservoir 28 to a desired level. The flow restrictor may comprise a reduced-diameter of the outlet passage 46 (in whole or in part), the diameter of the tubing 16 (FIG. 1), or a separate flow restrictor device positioned downstream from the fluid reservoir 28. Other suitable arrangements are also possible, including a combination of the above-mentioned flow restrictor arrangements.

With reference to FIGS. 2 and 6, the seal arrangement 32 is described in greater detail. The seal arrangement 32 desirably includes an annular recess, or groove 58, near an end of the support member 26. The recess 58 is defined by an outer surface of the support member 26 and, preferably, is substantially semi-circular in shape. A generally annular spring clip 60 is sized to be positionable onto the support member 26 and, preferably, cooperate with the recess 58 to create a seal between the sleeve 24 and the support member 26.

The spring clip 60 is configured to be movable from a relaxed position, or a free diameter of the clip 60, to a deflected position. In the relaxed position, an inner diameter of the spring clip 60 desirably is smaller than a diameter of the support member 26 with which the spring clip 60 is positioned. In the deflected position, the inner diameter of the clip 60, desirably, is large enough to pass over the elastic sleeve 24 and cylindrical support member 26 to permit assembly onto the infusion pump 12. Once released, the spring clip 60 returns toward the relaxed position. Preferably, the support member 26 is sized such that the spring clip 60 is prevented from returning to the fully relaxed position. Accordingly, the spring clip 60 exerts a squeezing force on the elastic sleeve 24 to create a seal between the sleeve 24 and the cylindrical support member 26 thereby defining an end of the fluid reservoir 28. As will be appreciated by one of skill in the art, the squeezing force developed by the spring clip 60 may be adjusted to a desired level by altering the relative sizes of the inner diameter of the spring clip 60 and the outer diameter of the corresponding portion of the support member 26, as well as by altering the properties of the spring clip 60 itself, such as the coil diameter of the clip 60, for example.

Desirably, the elastic sleeve 24 (and pouch 30, if provided) are biased into the recess 58 by the spring clip 60. Such an arrangement assists in defining and maintaining a proper position of the spring clip 60 relative to the support member 26. In addition, the deflection of the sleeve 24 into the recess 58 increases the effectiveness of the seal arrangement. Although only the inlet side 26*a* seal arrangement 32 is shown, preferably the outlet side 26*b* is constructed substantially similarly to that of the inlet side 26*a*.

A preferred spring clip 60 includes a generally annular body portion 62 ending in first and second ends 64, 66, respectively. Desirably, the clip 60 is substantially circular in cross-sectional shape and the body portion 62 overlaps itself along at least a portion of the annular region of the clip 60. Accordingly, movement of the first and second ends 64, 66 toward one another results in an increase in the inner diameter of the spring clip 60. Such an arrangement advantageously eases assembly of the spring clip 60 on to the cylindrical member 26 and the elastic sleeve 24.

Preferably, the spring clip 60 is constructed of metal, however, other suitable materials such as plastics may also be used. In one arrangement, the first and second ends 64, 66 extend in a generally radial direction relative to the annular body portion 62 and are of an initial length sufficient to permit grasping of the first and second ends 64, 66 by hand, with a tool, or by some other type of mechanical assistance. Such an arrangement permits the first and second ends 64, 66 to be squeezed toward one another to permit enlarging of the inner diameter of the clip 60 for assembly onto the infusion pump 12. Once the clip 60 is properly positioned, the first and second ends 64, 66 may be trimmed to a second, shorter length to prevent interference with the cap 34.

Desirably, the body portion 62 of the spring clip 60 is substantially non-elongating. That is, preferably, the spring clip 60 is substantially inelastic along the length of the body portion 62. As a result, the squeezing force exerted by the spring clip 60 occurs due to the stresses within the material of the clip 60, due to its being bent from an originally linear shape. Thus, the spring clip 60 behaves in a manner similar to a torsion spring. Accordingly, the spring clip 60 may be constructed from a material that is less susceptible to failure as a result of surface damage in comparison to a material that stretches along its length, such as an O-ring, or other elastomeric material.

Figure 7A:
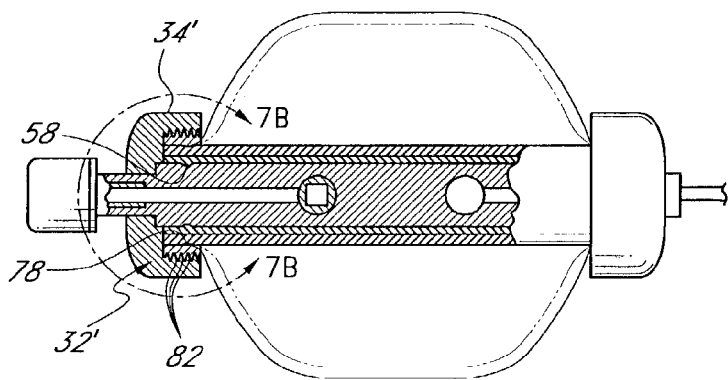
FIG. 7 is a cross-sectional view of an alternative infusion apparatus incorporating a split ring and cap assembly to create a seal between the elastic sleeve and cylindrical support member.
Figure 7B:
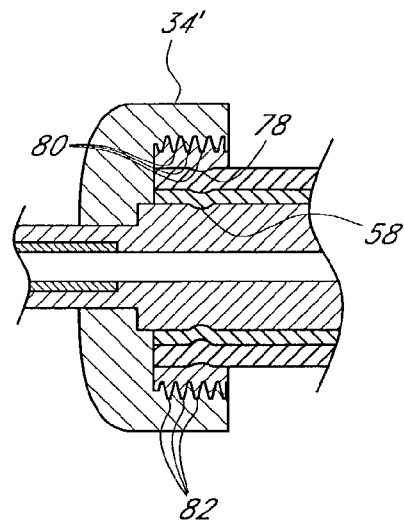
Figure 8:
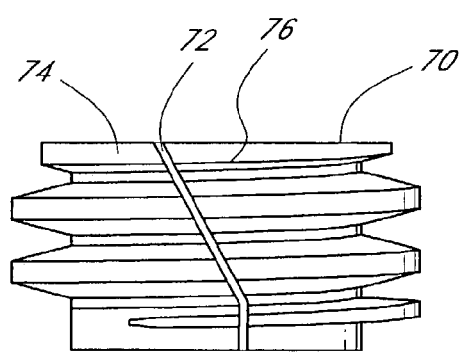
FIG. 8 is a side elevational view of the split ring illustrated as removed from the infusion apparatus of FIG. 7.

FIGS. 7 and 8 illustrate an alternative embodiment of the sealing arrangement 32 of FIGS. 1-6 and is generally referred to by reference numeral 32'. The infusion pump of FIGS. 7 and 8 is substantially similar to the infusion pump 12 of FIGS. 1 through 6 and, therefore, like reference numerals will be used to denote like components, except that a prime (') is added.

The seal arrangement 32' of FIGS. 7 and 8 includes a split ring 70 in place of the spring clamp 60 of the previous embodiment. The split ring 70 is substantially annular in shape and includes a gap 72 extending through the wall of the split ring 70 to define first and second ends 74, 76 of the split ring 70. As in the spring clamp 60 of the previous embodiment, desirably the split ring 70 is substantially non-elongating, or inelastic along its length.

An inner surface of the split ring 70 defines a generally annular protrusion 78, which acts as the inner surface of the spring clip 60 in the previous embodiment. Desirably, the protrusion 78 is substantially semi-circular in shape and is sized to cooperate with the recess, or groove 58', of the cylindrical support member 26' to create a seal between the elastic sleeve 24' and the support member 26'.

Preferably, an outer surface of the split ring 70 includes threads 80, which are configured to mate with internal threads 82 of the cap 34'. Thus, when the cap 34' is threaded on to the split ring 70, the split ring is compressed and exerts a sealing force on the elastic sleeve 24'. Although a threaded arrangement is preferred, other suitable means of applying a compressive force to the split ring 70 are also possible. For example, the cap 34' and split ring 70 may employ cooperating cam surfaces and a snap-fit arrangement which compresses the split ring 70 as the cap 34' is snapped on to the split ring 70. Other suitable arrangements apparent to those of skill in the art may also be used.

Both of the seal assembly embodiments described above are capable of providing a sufficient sealing force to the elastic sleeve 24, 24', while being more reliable than current seal assemblies, including O-ring type arrangements. Desirably, either embodiment provides a sealing force of at least twenty pounds. In addition, preferably, the spring clip 60 is configured to have a spring constant of at least ten pounds per inch. These values are preferred for common elastomeric infusion pumps utilizing an elastic sleeve member 24 and defining a fluid reservoir 28 of between about 50-100 milliliters. Accordingly, these values may differ for alternative infusion pump arrangements.

Although the present invention has been described in relation to a description of preferred embodiments, modifications and variations apparent to those of skilled in the art are considered to be within the scope of the present invention. Accordingly, the present invention should be defined only by the appended claims.

What is claimed is:

1. A method of assembling an infusion apparatus, comprising:

providing a support member at least partially defining an inlet and an outlet;

positioning an elastic sleeve over the support member, thereby defining a variable-volume fluid reservoir between the support member and the sleeve, the inlet and the outlet communicating with the fluid reservoir;

providing a pair of spring clips, each clip having a first end, a second end and a generally annular body portion extending between the first and second ends;

applying an opposing force to each of the first and second ends of one of the spring clips to deflect the spring clip into a deflected position and passing the spring clip over a first end of the support member and sleeve, releasing the first and second ends to permit the body portion to contact the sleeve and create a seal between the sleeve and the support member and thereby define a first end of the fluid reservoir;

applying an opposing force to each of the first and second ends of the other of the spring clips to deflect the spring clip into a deflected position and passing the spring clip over a second end of the support member and the sleeve, releasing the first and second ends to permit the body portion to contact the sleeve and create a seal between the sleeve and the support member and thereby define a second end of the fluid reservoir;

wherein the first and second ends of the spring clip have an initial length, additionally comprising the step of trimming the first and second ends to a shorter length after the respective spring clip is positioned onto the support member and sleeve.

2. The method of claim 1, additionally comprising the step of securing a cap to the support member, the cap including a side wall portion covering the first and second ends of the spring clip.

3. The method of claim 1, wherein an outer surface of the support member defines a pair of grooves spaced from one another, additionally comprising the step of positioning the spring clips such that the elastic sleeve is urged at least partially within the grooves.

4. An infusion apparatus, comprising:

an infusion pump including an elastic sleeve surrounding a support member, the sleeve and the support member cooperating to define a variable-volume fluid reservoir therebetween, the infusion pump including an inlet and an outlet in fluid communication with the fluid reservoir;

a pair of sealing assemblies, each assembly being configured to create a seal between the elastic sleeve and the support member to define first and second ends, respectively, of the fluid reservoir, each of the assemblies comprising a split ring and a cap, the split ring having a first end, a second end and a generally annular body portion extending between the first and second ends, the split ring being deflectable to an inner diameter sufficient to permit the split ring to pass over an end of the infusion pump, the cap being configured to apply a compressive force to the split ring, thereby deflecting the split ring to an inner diameter sufficient to create a seal between the elastic sleeve and the support member;

wherein each end portion of an outer surface of the support member defines an annular groove, each end of the elastic sleeve extending over the respective groove, an inner surface of the split ring defining a protrusion extending along the entire length of the body portion, the protrusion being sized and shaped to urge the elastic sleeve into the groove.

5. The infusion apparatus of claim 4, wherein the split ring and the cap comprise an interlocking thread arrangement, the cap being threadable onto the split ring to apply the compressive force to the split ring.

* * * * *